United States Patent
Matthews

(10) Patent No.: US 8,163,757 B2
(45) Date of Patent: Apr. 24, 2012

(54) IMMUNO INHIBITORY PYRAZOLONE COMPOUNDS

(75) Inventor: Ian Richard Matthews, Abingdon (GB)

(73) Assignee: MediGene AG, Martinsried (DE)

( * ) Notice: Subject to any disclaimer, the term of this patent is extended or adjusted under 35 U.S.C. 154(b) by 0 days.

(21) Appl. No.: 12/874,280

(22) Filed: Sep. 2, 2010

(65) Prior Publication Data

US 2010/0331342 A1 Dec. 30, 2010

Related U.S. Application Data

(62) Division of application No. 10/577,470, filed as application No. PCT/GB2004/004629 on Nov. 2, 2004, now Pat. No. 7,816,361.

(30) Foreign Application Priority Data

Nov. 4, 2003 (GB) .................................. 0325644.3

(51) Int. Cl.
*A61K 31/496* (2006.01)
*A61K 31/497* (2006.01)
*A61K 31/454* (2006.01)
*A61K 31/4152* (2006.01)
*C07D 401/14* (2006.01)
*C07D 403/12* (2006.01)
*C07D 231/22* (2006.01)
*A61P 37/02* (2006.01)

(52) U.S. Cl. ............. 514/254.05; 514/255.05; 514/326; 514/407; 544/371; 544/405; 546/209; 548/371.1

(58) Field of Classification Search ........................ None
See application file for complete search history.

(56) References Cited

U.S. PATENT DOCUMENTS

| 3,576,637 | A | 4/1971 | Suga et al. |
| 4,591,589 | A | 5/1986 | Gasc et al. |
| 5,061,705 | A | 10/1991 | Wuest et al. |
| 7,276,505 | B2 | 10/2007 | Matthews |

FOREIGN PATENT DOCUMENTS

| EP | 0255892 | 2/1988 |
| EP | 0269030 | 6/1988 |
| GB | 629412 | 9/1949 |
| JP | 45026736 | 9/1970 |
| WO | 97/34893 | 9/1997 |
| WO | 03/004495 | 1/2003 |
| WO | 2004/048378 | 6/2004 |
| WO | 2004/055014 | 7/2004 |
| WO | 2004/081011 | 9/2004 |

OTHER PUBLICATIONS

Appel & Brossart, "Development of Novel Compounds to Treat Autoimmune and Inflammatory Diseases and Graft Versus Host Reactions," Endocrin. Metab. Immune Disord. Drug Targets No. 7, pp. 93-97, 2007.

Brumeanu et al., "Down-regulation of autoreactive T-cells by HMG CoA reductase inhibitors," Clin. Immunol. vol. 119, pp. 1-12, 2006.
Chitale & Moots, "Abatacept: the first T lymphocyte co-stimulation modulator, for the treatment of rheumatoid arthritis," Expert. Opin. Biol. Ther., vol. 8, pp. 115-122, 2008.
Choy, "T Cells in Psoriatic Arthritis," Curr. Rheumatol. Rep. vol. 6, pp. 437-441, 2007.
Cope et al., "The central role of T cells in rheumatoid arthritis," Clin. Exp. Rheumatol., vol. 25, pp. S4-S11, 2007.
Dubey et al., "Costimulatory requirements of naive CD4+ T cells. ICAM-1 or B7-1 can costimulate Naïve CD4 T Cell Activation but Both Are Required for Optimum Response," J Immunol., vol. 155, pp. 45-57, 1995.
Gimmi et al., "Human T-cell clonal anergy is induced by antigen presentation in the absence of B7 costimulation," Immunology, vol. 90, pp. 6586-6590, Jul. 1993.
Kristensen et al., "The number needed to treat for adalimumab, etanercept, and infliximab based on ACR50 response in three randomized controlled trials on established rheumatoid arthritis: a systematic literature review," Scand. J. Rheumatol., vol. 36, pp. 411-417, 2007.
Linsley et al., "Binding of the B Cell Activation Antigen B7 to CD28 Costimulates T Cell Proliferation and Interleukin 2 mRNA Accumulation," J. Exp. Med. vol. 173, pp. 721-730, Mar. 1991.
Mallone & Endert, "T Cells in the Pathogenesis of Type 1 Diabetes," Curr. Diab. Rep., vol. 8, pp. 101-106, 2008.
Suresh et al., "Role of CD28-B7 Interactions in Generation and Maintenance of CD8 T Cell Memory," The Journal of Immunology, vol. 167: pp. 5565-5573, 2001.
Weiss et al., ."Role of CD28-B7 Interactions in Generation and Maintenance of CD8 T Cell Memory," Neuroimmunol. vol. 191, pp. 79-85, 2007.
Medigene Press Release, "RhuDex(TM) Clinical Development to Continue Following Feedback from Regulatory Authorities," Oct. 5, 2009.

(Continued)

*Primary Examiner* — Kamal Saeed
(74) *Attorney, Agent, or Firm* — Banner & Witcoff, Ltd.

(57) ABSTRACT

The present invention relates to compounds of formula (IA) or (IB) or pharmaceutically or veterinarily acceptable salt thereof:

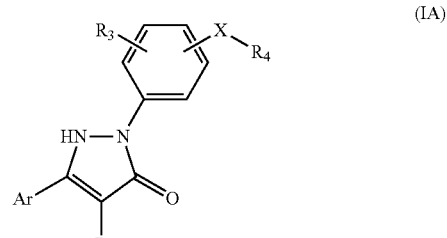

(IA)

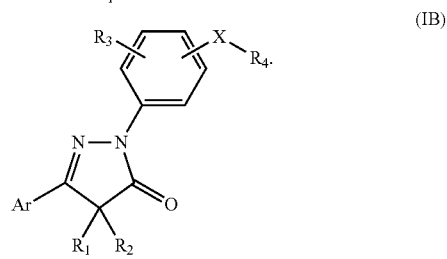

(IB)

16 Claims, No Drawings

OTHER PUBLICATIONS

Collins et al., "The interaction properties of costimulatory molecules revisited," Immunity, vol. 17, pp. 201-210, 2002.

Lenschow et al., "CD28/B7 system of T cell costimulation," Annu. Rev. Immunol., vol. 14, pp. 233-258, 1996.

Huxley et al., "High-affinity small molecule inhibitors of T cell costimulation," Chem. Biol., vol. 11, pp. 1651-1658, 2004.

Salomon et al., B7/CD28 costimulation is essential for the homeostasis of the CD4+CD25+ immunoregulatory T cells that control autoimmune diabetes; Immunity, vol. 12, pp. 431-440, 2000.

West, "Solid state chemistry and its applications," Wiley & Sons, New York, book Chapter 10, pp. 358-359, 1988.

Griesser, "The Importance of Solvates," Polymorphism in the Pharmazuetical Industry, Chapter 8, pp. 211-230, 2006.

Strieth et al., "Paclitaxel encapsulated in cationic liposomes increases tumor microvessel leakiness and improves therapeutic efficacy in combination with Cisplatin," Clin Cancer Res., vol. 14, No. 14, pp. 4603-4611, 2008.

Lukes et al., "Oral feeding with pig peripheral lymphocytes decreases the xenogeneic delayed type hypersensitivity reaction in galactosyltransferase knockout mice," Abstract, Transplant Proc., vol. 37, No. 8, pp. 3327-3331, 2005.

Strieth et al., "Tumor-selective vessel occlusions by platelets after vascular targeting chemotherapy using paclitaxel encapsulated in cationic liposomes," Int J Cancer, vol. 122, No. 2, pp. 452-460, 2008.

Ames & Bull, "Preparation of cinnoline-3, 4-dicarbonitrile and -dicarboxylic acid," Tetrahedron, vol. 37, No. 14, pp. 2489-2491, 1981.

Picciola G et al: "Heterocyclic compounds with potential anti inflammatory activity containing 4-aminophenylalkanoic acid moieties. V. 2, 4-Dihydro-3H-pyrazol-3-one derivatives" Farmaco Edizione Scientifica., vol. 39, No. 4, 1984, pp. 371-378, XP009043142, Itsocieta Chimica Italiana, Pavia tables I, II compound 18902.

Database Beilstein 1992, XP002315401, Database accession No. 697617 (CNR) BRN 343115, 325012, 361725, 361896 & J. Prakt. Chem., vol. 2-121, 1929, p. 201.

Byun J-W et al "Preparation of polymer-bound pyrazolone active esters for combinatorial chemistry" Tetrahedron Letters., vol. 44, Oct. 27, 2003, pp. 8063-8067, XP004461054 Nlelsevier Science Publishers, Amsterdam.

Database Beilstein 1993, XP002315402, Database accession No. 695619 (CNR) BRN 695619, 312421 & Justus Liebigs Ann. Chem., vol. 373, 1910, p. 167.

Database Caplus Chemical Abstracts Service, Columbus, Ohio, US: 1971, XP002315403, Database accession No. 74:87973 (DN) RN 21749-59-7.

IMMUNO INHIBITORY PYRAZOLONE COMPOUNDS

This application is a divisional application of U.S. Ser. No. 10/577,470, with a 371(c) filing date of Jan. 11, 2007, now allowed, which is a U.S. National Stage application of co-pending PCT application PCT/GB2004/004629, filed Nov. 2, 2004, expired, which claims the priority of Great Britain Patent Application No. 0325644.3, filed Nov. 4, 2003. These applications are incorporated herein by reference in its entirety.

The present invention relates to pyrazolone compounds, to methods for their preparation, to compositions containing them, and to methods and use for clinical treatment of medical conditions which may benefit from immunomodulation, e.g. rheumatoid arthritis, multiple sclerosis, diabetes, asthma, transplantation, systemic lupus erythematosis and psoriasis. More particularly the present invention relates to pyrazolone compounds, which are CD80 antagonists capable of inhibiting the interactions between CD80 and CD28.

BACKGROUND TO THE INVENTION

The immune system possesses the ability to control the homeostasis between the activation and inactivation of lymphocytes through various regulatory mechanisms during and after an immune response. Among these are mechanisms that specifically inhibit and/or turn off an immune response. Thus, when an antigen is presented by MHC molecules to the T-cell receptor, the T-cells become properly activated only in the presence of additional co-stimulatory signals. In the absence of these accessory signals there is no lymphocyte activation and either a state of functional inactivation termed anergy or tolerance is induced, or the T-cell is specifically deleted by apoptosis.

One such co-stimulatory signal involves interaction of CD80 on specialised antigen-presenting cells with CD28 on T-cells, and this signal has been demonstrated to be essential for full T-cell activation. (Lenschow et al. (1996) *Annu. Rev. Immunol.*, 14, 233-258). It would therefore be desirable to provide compounds which inhibit this CD80/CD28 interaction.

DETAILED DESCRIPTION OF THE INVENTION

According to the present invention there is provided a compound of formula (IA) or (IB) or a pharmaceutically or veterinarily acceptable salt, hydrate or solvate thereof:

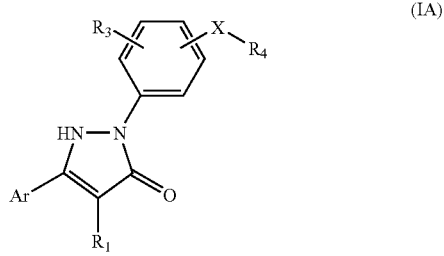

(IA)

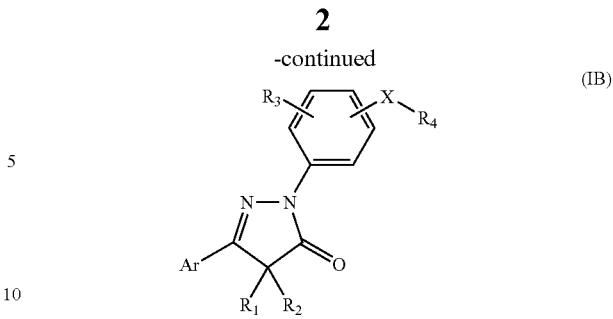

(IB)

wherein

Ar represents an optionally substituted monocyclic or bicyclic aromatic or heteroaromatic group having from 5 to 10 ring atoms, $R_1$ and $R_2$ independently represent H, or $C_1$-$C_6$ alkyl;

$R_3$ represents H; F; Cl; Br; —$NO_2$; —CN; $C_1$-$C_6$ alkyl optionally substituted by F or Cl; or $C_1$-$C_6$ alkoxy optionally substituted by F;

$R_4$ represents a carboxylic acid group (—COOH) or an ester thereof, or —C(=O)$NR_6R_7$, —$NR_7$C(=O)$R_6$, —$NR_7$C(=O)$OR_6$, —NHC(=O)$NR_7R_6$ or —NHC(=S)$NR_7R_6$ wherein $R_6$ represents H, or a radical of formula -(Alk)$_m$-Q wherein m is 0 or 1

Alk is an optionally substituted divalent straight or branched $C_1$-$C_{12}$ alkylene, or $C_2$-$C_{12}$ alkenylene, or $C_2$-$C_{12}$ alkynylene radical or a divalent $C_3$-$C_{12}$ carbocyclic radical, any of which radicals may be interrupted by one or more —O—, —S— or —N($R_8$)— radicals wherein $R_8$ represents H or $C_1$-$C_4$ alkyl, $C_3$-$C_4$ alkenyl, $C_3$-$C_4$ alkynyl, or $C_3$-$C_8$ cycloalkyl, and Q represents H; —$CF_3$; —OH; —SH; —$NR_8R_6$ wherein each $R_8$ may be the same or different, or form a ring when taken together with the nitrogen to which they are attached; an ester group; or an optionally substituted aryl, aryloxy, cycloalkyl, cycloalkenyl or heterocyclic group; and $R_7$ represents H or $C_1$-$C_6$ alkyl; or when taken together with the atom or atoms to which they are attached $R_6$ and $R_7$ form a monocyclic heterocyclic ring having 5, 6 or 7 ring atoms; and X represents a bond or a divalent radical of formula —(Z)$_n$-(Alk)- or -(Alk)-(Z)$_n$— wherein Z represents —O—, —S— or —NH—, Alk is as defined in relation to $R_6$ and n is 0 or 1.

Compounds (IA) may exist in the form of tautomers (IA$^1$):

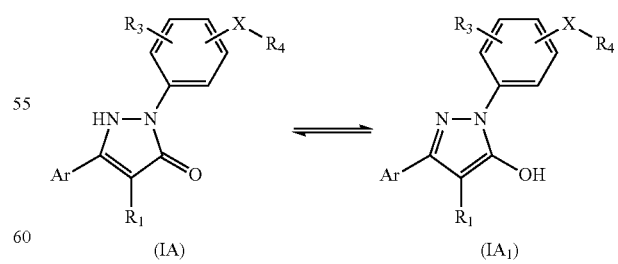

(IA)        (IA$_1$)

Hereafter, the compounds (IA) of the invention may be represented and referred to in either tautomeric form and it is to be understood that any and all tautomeric forms of structures (IA) and (IB), in particular (IA$^1$), are included in the invention.

Compounds of general formula (IA) and (IB) are CD80 antagonists. They inhibit the interaction between CD80 and CD28 and thus the activation of T cells, thereby modulating the immune response.

Accordingly the invention also includes:

(i) a compound of formula (IA) or (IB) or a pharmaceutically or veterinarily acceptable salt thereof for use in the treatment of conditions which benefit from immunomodulation.

(ii) the use of a compound of formula (IA) or (IB) or a pharmaceutically or veterinarily acceptable salt thereof in the manufacture of a medicament for the treatment of conditions which benefit from immunomodulation.

(iii) a method of immunomodulation in mammals, including humans, comprising administration to a mammal in need of such treatment an immunomodulatory effective dose of a compound of formula (IA) or (IB) or a pharmaceutically or veterinarily acceptable salt thereof.

(iv) a pharmaceutical or veterinary composition comprising a compound of formula (IA) or (IB) or a pharmaceutically or veterinarily acceptable salt thereof together with a pharmaceutically or veterinarily acceptable excipient or carrier.

Conditions which Benefit from Immunomodulation Include:
Acute disseminated encephalomyelitis
Adrenal insufficiency
Allergic angiitis and granulomatosis
Amylodosis
Ankylosing spondylitis
Asthma
Autoimmune Addison's disease
Autoimmune alopecia
Autoimmune chronic active hepatitis
Autoimmune haemolytic anaemia
Autoimmune Neutrogena
Autoimmune thrombocytopenic purpura
Behçet's disease
Cerebellar degeneration
Chronic active hepatitis
Chronic inflammatory demyelinating polyradiculoneuropathy
Chronic neuropathy with monoclonal gammopathy
Classic polyarteritis nodosa
Congenital adrenal hyperplasia
Cryopathies
Dermatitis herpetiformis
Diabetes
Eaton-Lambert myasthenic syndrome
Encephalomyelitis
Epidermolysis bullosa acquisita
Erythema nodosa
Gluten-sensitive enteropathy
Goodpasture's syndrome
Guillain-Barre syndrome
Hashimoto's thyroiditis
Hyperthyroidism
Idiopathic hemachromatosis
Idiopathic membranous glomerulonephritis
Isolated vasculitis of the central nervous system
Kawasaki's disease
Minimal change renal disease
Miscellaneous vasculitides
Mixed connective tissue disease
Multifocal motor neuropathy with conduction block
Multiple sclerosis
Myasthenia gravis
Opsoclonus-myoclonus syndrome
Pemphigoid
Pemphigus
pernicious anaemia
Polymyositis/dermatomyositis
Post-infective arthritides
Primary biliary sclerosis
Psoriasis
Reactive arthritides
Reiter's disease
Retinopathy
Rheumatoid arthritis
Sclerosing cholangitis
Sjögren's syndrome
Stiff-man syndrome
Subacute thyroiditis
Systemic lupus erythematosus
Systemic necrotizing vasculitides
Systemic sclerosis (scleroderma)
Takayasu's arteritis
Temporal arteritis
Thromboangiitis obliterans
Type I and type II autoimmune polyglandular syndrome
Ulcerative colitis
Uveitis
Wegener's granulomatosis As used herein, the term "ester" refers to a group of the form —COOR, wherein R is a radical notionally derived from the alcohol ROH. Examples of ester groups include the physiologically hydrolysable esters such as the methyl, ethyl, n- and iso-propyl, n-, sec- and tert-butyl, and benzyl esters.

As used herein the term "alkylene" refers to a straight or branched alkyl chain having two unsatisfied valencies, for example —$CH_2$—, —$CH_2CH_2$—, —$CH_2CH_2CH_2$—, —$CH(CH_3)CH_2$—, —$CH(CH_2CH_3)CH_2CH_2CH_2$—, and —$C(CH_3)_3$.

As used herein the term "alkenylene" refers to a straight or branched alkenyl chain having two unsatisfied valencies, for example —CH=CH—, —$CH_2$CH=CH—, —$C(CH_3)$=CH—, and —$CH(CH_2CH_3)$CH=$CHCH_2$—.

As used herein the term "alkynylene" refers to a straight or branched alkynyl chain having two unsatisfied valencies, for example —C≡C—, —$CH_2$C≡C—, and —$CH(CH_2CH_3)$C≡$CCH_2$—.

Unless otherwise specified in the context in which it occurs, the term "substituted" as applied to any moiety herein means substituted with at least one substituent, for example selected from ($C_1$-$C_6$)alkyl, trifluoromethyl, ($C_1$-$C_6$)alkoxy (including the special case where a ring is substituted on adjacent ring C atoms by alkylenedioxy such as methylenedioxy or ethylenedioxy), trifluoromethoxy, ($C_1$-$C_6$)alkylthio, phenyl, benzyl, phenoxy, benzyloxy, hydroxy, mercapto, amino, fluoro, chloro, bromo, cyano, nitro, oxo, —COOH, —$SO_2$OH, —$CONH_2$, —$SO_2NH_2$, —$COR^A$, —$COOR^A$, —$SO_2OR^A$, —$NHCOR^A$, —$NHSO_2R^A$, —$CONHR^A$, —$SO_2NHR^A$, —$NHR^A$, —$NR^AR^B$, —$CONR^AR^B$ or —$SO_2NR^AR^B$ wherein $R^A$ and $R^B$ are independently a ($C_1$-$C_6$)alkyl or $C_2$-$C_6$ alkoxy group or a monocyclic carbocyclic or heterocyclic group of from 5-7 ring members, or $R^A$ and $R^B$ form a ring when taken together with the nitrogen to which they are attached. In the case where "substituted" means substituted by phenyl, benzyl, phenoxy, or benzyloxy, the phenyl ring thereof may itself be substituted with any of the foregoing, except phenyl, benzyl, phenoxy, or benzyloxy.

As used herein the term "aryl" refers to a mono-, bi- or tri-cyclic carbocyclic aromatic radical, and to two such radicals covalently linked to each other, Illustrative of such radicals are phenyl, biphenyl and napthyl.

As used herein the unqualified term "carbocyclyl" or "carbocyclic" includes aryl, cycloalkyl and cycloalkenyl and refers to a ring system (monocyclic, bicyclic, tricyclic or bridged) whose ring atoms are all carbon.

As used herein the unqualified term "cycloalkyl" refers to a carbocyclic ring system which contains only single bonds between ring carbons.

As used herein the unqualified term "cycloalkenyl" refers to a carbocyclic ring system which contains at least one double bond between a pair of ring carbons.

As used herein the term "heteroaryl" refers to a mono-, bi- or tri-cyclic aromatic radical containing one or more heteroatoms selected from S, N and O. Illustrative of such radicals are thienyl, benzothienyl, furyl, benzofuryl, pyrrolyl, imidazolyl, benzimidazolyl, thiazolyl, benzthiazolyl, isothiazolyl, benzisothiazolyl, pyrazolyl, oxazolyl, benzoxazolyl, isoxazolyl, benzisoxazolyl, isothiazolyl, triazolyl, benztriazolyl, thiadiazolyl, oxadiazolyl, pyridinyl, pyridazinyl, pyrimidinyl, pyrazinyl, triazinyl, indolyl and indazolyl.

As used herein the unqualified term "heterocyclyl" or "heterocyclic" includes "heteroaryl" as defined above, and in particular means a mono-, bi- or tri-cyclic or bridged non-aromatic radical containing one or more heteroatoms selected from S, N and O, and to groups consisting of a monocyclic non-aromatic radical containing one or more such heteroatoms which is covalently linked to another such radical or to a monocyclic carbocyclic radical. Illustrative of such radicals are pyrrolyl, furanyl, thienyl, piperidinyl, imidazolyl, oxazolyl, isoxazolyl, thiazolyl, thiadiazolyl, pyrazolyl, pyridinyl, pyrrolidinyl, pyrimidinyl, morpholinyl, piperazinyl, indolyl, morpholinyl, benzofuranyl, pyranyl, isoxazolyl, benzimidazolyl, methylenedioxyphenyl, ethylenedioxyphenyl, maleimido and succinimido groups.

Some compounds of the invention contain one or more chiral centres because of the presence of asymmetric carbon atoms. The presence of asymmetric carbon atoms gives rise to stereoisomers or diastereoisomers with R or S stereochemistry at each chiral centre. The invention includes all such stereoisomers and diastereoisomers and mixtures thereof.

Salts of salt forming compounds of the invention include physiologically acceptable acid addition salts for example hydrochlorides, hydrobromides, sulphates, methane sulphonates, p-toluenesulphonates, phosphates, acetates, citrates, succinates, lactates, tartrates, fumarates and maleates; and base addition salts, for example sodium, potassium, magnesium, and calcium salts.

Methods

Compounds of the invention of formula (IA) wherein $R_1$ is hydrogen and wherein $R_4$ represents an amide group —C(=O)NR$_6$R$_7$ may be prepared by reaction of the appropriate amine HNR$_6$R$_7$ with a compound of formula (II) to amidate the carboxylic acid group:

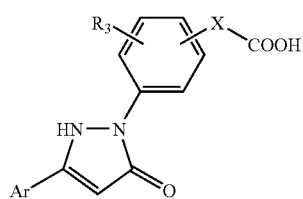

(II)

the symbols Ar, $R_3$, X, $R_6$ and $R_7$ being as defined in relation to formula (I) above.

Compounds (II) (ie compounds (IA) of the invention wherein $R_1$ is hydrogen and $R_4$ is a carboxylic acid group) may be prepared by reaction of a compound of formula (III) with a hydrazine of formula (IV):

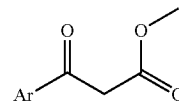

(III)

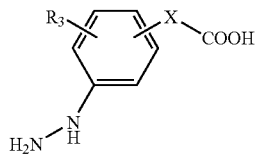

(IV)

This reaction may result in the preparation of a mixture of the position isomers (IIA) and (IIB):

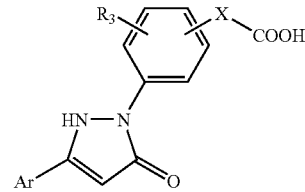

(IIA)

(IIB)

from which the desired isomer (IIA) may be separated.

Compounds (IA) wherein $R_1$ is hydrogen and $R_4$ is an amide (—C(=O)NR$_6$R$_7$) or ester group may also be prepared from intermediate (III) by reaction with the appropriate hydrazine (IVA)

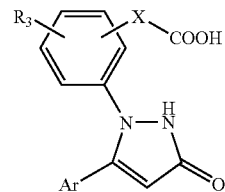

(IVA)

wherein $R_4$ is the amide or ester group. Again the reaction may result in a mixture of the ester analogues of the carboxylic acids (IIA) and (IIB), from which the desired ester isomer (I) may be separated. Alternatively, the carboxylic acid compound (II) may simply be esterified, or amidated (the latter being a route referred to above).

Compounds (IA) wherein $R_1$ is hydrogen and $R_4$ is a "reverse amide" group —NR$_7$C(=O)R$_6$ may be prepared by Curtius rearrangement (see Ninomiya, K.; Shioiri, T.; Yamada, S. Tetrahedron (1974), 30(14), 2151-7) of the carboxylic acid (II) to the isocyanate (V)

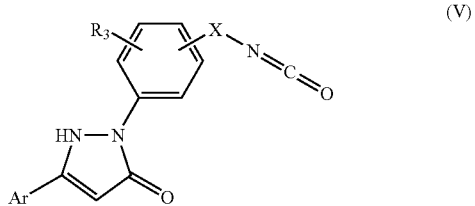

followed by hydrolysis of the isocyanate group to an amino group and acylation of the amino group with, for example, the acid chloride Cl—C(=O)$R_6$. In cases where $R_7$ is not hydrogen, the $R_7$ substituent may be introduced after the isocyanate reduction step or after the acylation step.

Compounds (IA) wherein $R_1$ is hydrogen and $R_4$ is a urea group —NHC(=O)NH$R_6$ or thiourea group —NHC(=S)NH$R_6$ may also be prepared from the isocyanate (V) or the corresponding isothiocyanate by reaction with the appropriate amine $H_2NR_6$.

Compounds (I) wherein $R_4$ is a carbamate group —$NR_7$C(=O)O$R_6$ may be prepared by the reaction of the isocyanate with an appropriate alcohol $R_6$OH.

Compounds (IA) and (IB) wherein $R_1$ and $R_2$ are $C_1$-$C_6$ alkyl may be prepared by alkylation of the corresponding compound (IA) wherein $R_1$ is hydrogen.

Further details of the synthetic methods for the preparation of compounds (I) of the invention, and intermediates such as (III), may be found in the examples herein.

In the compounds of the invention:

$R_1$ and $R_2$ independently represent hydrogen or $C_1$-$C_6$ alkyl, such as methyl, ethyl, n- or iso-propyl, n-, sec- or tert-butyl.

$R_4$ represents a carboxylic acid group (—COOH) or an ester thereof, or —C(=O)$NR_6R_7$, —$NR_7$C(=O)$R_6$, —$NR_7$C(=O)O$R_6$ or —NHC(=O)NH$R_6$, all as defined above.

When $R_4$ is an ester group, examples include those of formula —COOR wherein R is methyl, ethyl n- or iso-propyl, n-, sec- or tert-butyl, or benzyl ester.

$R_6$, when present, represents H, or a radical of formula -(Alk)$_m$-Q wherein m, Alk and Q being as defined above. When m is 1, Alk may be, for example a straight or branched $C_1$-$C_6$ alkylene radical, such as —$CH_2$—, —$CH_2CH_2$—, —$CH_2CH_2CH_2$—, and —$CH_2CH(CH_3)CH_2$—. Alk may also be, for example, a divalent cyclopropylene, cyclopentylene or cyclohexylene radical. The radical Alk may be optionally substituted by, for example, OH, oxo, $CF_3$, methoxy or ethoxy. The radical Alk may optionally contain a hetero atom, for example in the form of an ether, thioether or amino linkage.

The group Q may represent, for example, hydrogen; —$NR_8R_8$ wherein each $R_8$ may be the same or different and selected from hydrogen, methyl, ethyl, n- or isopropyl or tert-butyl; an ester group for example a methyl, ethyl or benzyl ester; or an optionally substituted aryl, aryloxy, cycloalkyl, cycloalkenyl or heterocyclic group, for example phenyl, phenoxy, cyclopentyl, cyclohexyl, furyl, thienyl, piperidyl, or piperazinyl group.

$R_7$ when present represents H or $C_1$-$C_6$ alkyl, for example methyl, ethyl n- or iso-propyl, n-, sec- or tert-butyl; or when taken together with the atom or atoms to which they are attached $R_6$ and $R_7$ form a monocyclic heterocyclic ring having 5, 6 or 7 ring atoms;

Ar may be, for example, optionally substituted phenyl, 2-, 3-, or 4-pyridyl, 2-, or 3-furyl, 2-, or 3-thienyl, benzfur-2-yl, or benzothien-2-yl. Optional substituents in Ar include, for example F, Cl, methyl, methoxy, or methylenedioxy. Currently it is preferred that Ar is 3-fluorophenyl and 2-, or 3-furyl, $R_3$ may be, for example, H, F, Cl, methyl, methoxy, or methylenedioxy. Currently it is preferred that $R_3$ is H;

X may be, for example a bond, or a —$CH_2$— or —$CH_2CH_2$— radical. A bond is presently preferred.

A specific preferred subset of compounds of the invention has formula (IC):

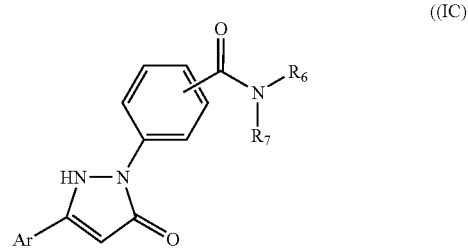

wherein Ar, $R_6$ and $R_7$ are as specified above. In this subset, the radical —C(=O)$NR_6R_7$ may be in the 4-position of the phenyl ring. This subset includes in particular, compounds wherein $R_7$ is hydrogen and $R_6$ is -AlkN$R_6R_6$ wherein the $R_8$ groups are is as defined above.

Specific compounds of the invention include those of the Examples herein.

As mentioned above, the invention includes pharmaceutical or veterinary composition comprising a compound of formula (I) or a pharmaceutically or veterinarily acceptable salt thereof together with a pharmaceutically or veterinarily acceptable excipient or carrier. In such compositions, it will be understood that the specific dose level for any particular patient will depend upon a variety of factors including the activity of the specific compound employed, the age, body weight, general health, sex, diet, time of administration, route of administration, rate of excretion, drug combination and the cause and severity of the particular disease undergoing therapy. Optimum dose levels and frequency of dosing will be determined by clinical trial.

The compounds with which the invention is concerned may be prepared for administration by any route consistent with their pharmacokinetic properties. The orally administrable compositions may be in the form of tablets, capsules, powders, granules, lozenges, liquid or gel preparations, such as oral, topical, or sterile parenteral solutions or suspensions. Tablets and capsules for oral administration may be in unit dose presentation form, and may contain conventional excipients such as binding agents, for example syrup, acacia, gelatin, sorbitol, tragacanth, or polyvinyl-pyrrolidone; fillers for example lactose, sugar, maize-starch, calcium phosphate, sorbitol or glycine; tabletting lubricant, for example magnesium stearate, talc, polyethylene glycol or silica; disintegrants for example potato starch, or acceptable wetting agents such as sodium lauryl sulphate. The tablets may be coated according to methods well known in normal pharmaceutical practice. Oral liquid preparations may be in the form of, for example, aqueous or oily suspensions, solutions, emulsions, syrups or elixirs, or may be presented as a dry product for reconstitution with water or other suitable vehicle before use. Such liquid preparations may contain conventional additives such as suspending agents, for example sorbitol, syrup, methyl cellulose, glucose syrup, gelatin hydrogenated edible fats; emulsifying agents, for example lecithin, sorbitan monooleate, or acacia; non-aqueous vehicles (which may include edible oils), for example almond oil, fractionated coconut oil, oily esters such as glycerine, propylene glycol, or ethyl alcohol; preservatives, for example methyl or propyl p-hydroxybenzoate or sorbic acid, and if desired conventional flavouring or colouring agents.

For topical application to the skin, the drug may be made up into a cream, lotion or ointment. Cream or ointment formulations which may be used for the drug are conventional formulations well known in the art, for example as described in standard textbooks of pharmaceutics such as the British Pharmacopoeia.

For topical application to the eye, the drug may be made up into a solution or suspension in a suitable sterile aqueous or non aqueous vehicle. Additives, for instance buffers such as sodium metabisulphite or disodium edeate; preservatives including bactericidal and fungicidal agents such as phenyl mercuric acetate or nitrate, benzalkonium chloride or chlorhexidine, and thickening agents such as hypromellose may also be included.

The active ingredient may also be administered parenterally in a sterile medium. Depending on the vehicle and concentration used, the drug can either be suspended or dissolved in the vehicle. Advantageously, adjuvants such as a local anaesthetic, preservative and buffering agents can be dissolved in the vehicle.

Embodiments of the invention are described in the following non-limiting Examples:

The following abbreviations are used in the experimental descriptions:

| DMF | Dimethyl formamide |
| DMA | Dimethyl acetamide |
| DMSO | Dimethyl sulphoxide |
| THF | Tetrahydrofuran |
| HBTU | O-Benzotriazol-1-yl-N,N,N',N'-tetramethyluronium hexafluorophosphate |
| HPLC | High performance liquid chromatography |
| LCMS | Liquid chromatography mass spectrum |
| NMR | Nuclear magnetic resonance spectroscopy |

Example 1

4-(5-oxo-3-pyrazin-2-yl-2,5-dihydro-pyrazol-1-yl)-N-(1,2,2,6,6-pentamethyl-piperidin-4-yl)-benzamide

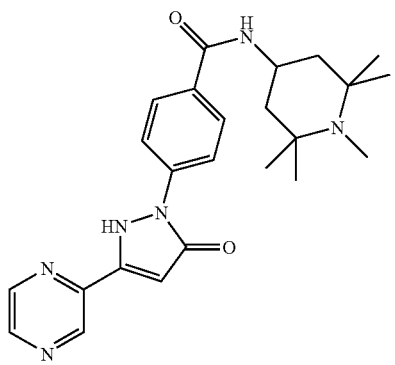

Step 1: Preparation of 4-(N'-tert-Butoxycarbonyl-hydrazino)-benzoic acid

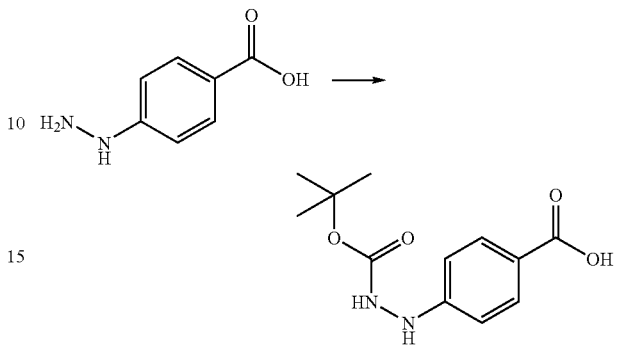

To a deep red solution of p-hydrazinobenzoic acid (32.86 mmol, 5.00 g) in 2M NaOH (100 ml) and THF (70 ml) was added di-tertbutyl dicarbonate (2.0 eq, 65.72 mmol, 14.34 g). This was stirred at rt over a weekend. Another aliquot of di-tertbutyl dicarbonate (3.5 g) was added to the reaction mixture, and this stirred at room temp for a further 24 hours. A further 0.5 eq p-hydrazinobenzoic acid added to the reaction mixture. This was then stirred for a further 24 hours. 10% citric acid solution was added until a pH of 4 was obtained. The product was then extracted with ethyl acetate, the organics washed with brine, and then dried over Na$_2$SO$_4$. Concentration in vacuo afforded a pale yellow oil, containing residual tert-BuOH. Hexane was added to the mixture. Precipitation was observed and the solids were collected by filtration, washed with hexane and dried under vacuum at 35° C. An orange powder was obtained (8.40 g).

Step 2: Preparation of N'-[1,2,2,6,6-Pentamethyl-piperidin-4-ylcarbamoyl)-phenyl]-hydrazinecarboxylic acid tert-butyl ester

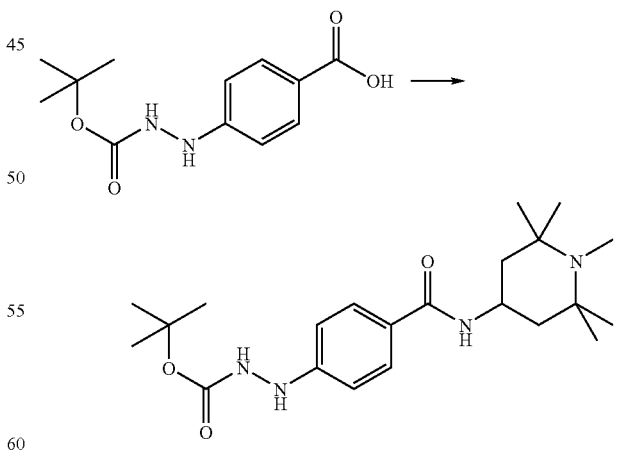

To a solution of 4-(N'-tert-Butoxycarbonyl-hydrazino)-benzoic acid (4.452 g) in DMA (30 ml) was added disopropyl ethyl amine (6.16 ml) and HBTU (6.69 g) with stirring at room temp. 4-Amino-1,2,2,6,6-pentamethylpiperidine (3 g) was then added to the stirred solution. Stirring continued at room temp for 4 hrs. The solution was partitioned between ethyl acetate (6×20 ml) and water. The organic fraction was taken, washed with brine, dried over MgSO₄ and the solvent removed under vacuum. This revealed a deep orange oil (6.2 g, 86%).

Step 3: Preparation of 4-Hydrazino-N-(1,2,2,6,6-pentamethyl-piperidin-4-yl)-benzamide

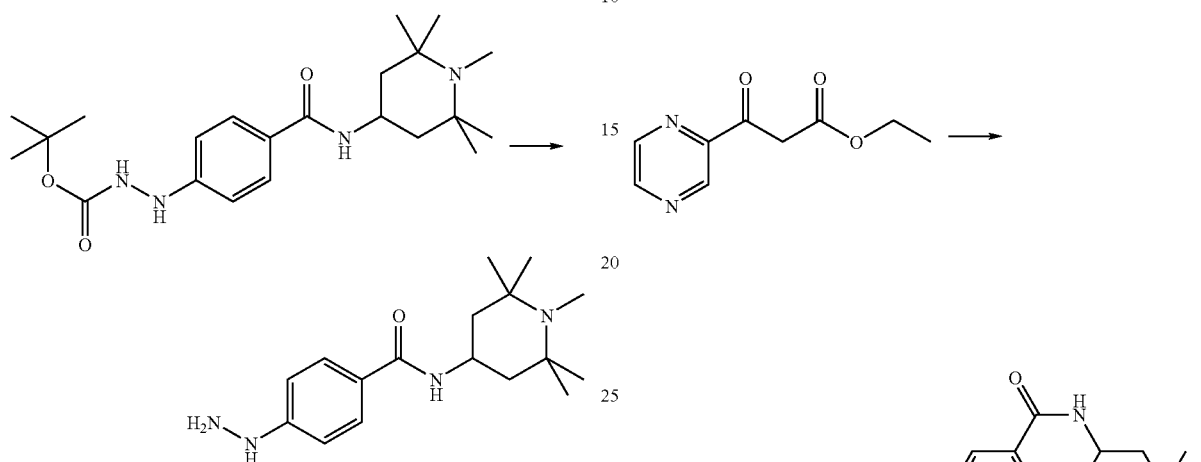

N'-[4-(1,2,2,6,6-Pentamethyl-piperidin-4-ylcarbamoyl)-phenyl]-hydrazinecarboxylic acid tert-butyl ester was dissolved in 4M HCl in dioxane (30 ml) and left to stir for 1-2 hrs. The solution went quickly from a deep orange colour to a bright orange colour. After 1 hr reaction time, the solvent was removed under vacuum to reveal an orange oil that under a vacuum for several minutes crystallized out to give orange crystals in a sticky orange oil. Yield: 4.68 g, 87%.

Step 4: Preparation of 3-Oxo-3-pyrazin-2-yl-propionic acid, ethyl ester

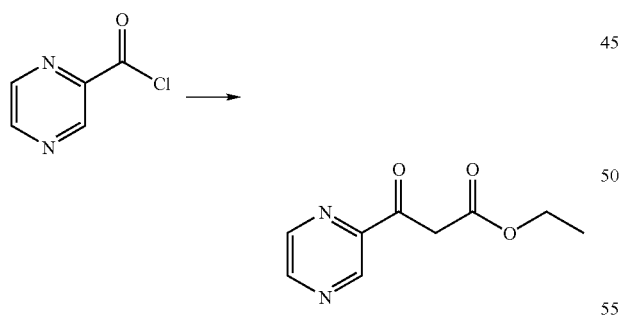

To a stirred solution of diethyl malonate (1.25 ml, 1.32 g) in THF (20 ml) under an atmosphere of nitrogen at −60° C. was added nbutyl lithium (2.5 M, 9 ml) dropwise over 15 min, keeping the temperature constant. The reaction became a cloudy white colour from the formation of the di-lithium salt then became yellowish. After 10 min, the reaction was cooled to −78° C., when a solution of pyrazine-2-carbonyl chloride (0.5 g, dark purple solution in THF (10 ml)) was added dropwise over 15 min. The reaction then warmed to −45° C. and stirred for 1 h. The reaction was then poured into 1M HCl solution (35 ml) with stirring. This was transferred to a separating funnel, and extracted with CH₂Cl₂ (2×150 ml). The combined organic layers were then washed with sat. NaCO₃ soln (1×30 ml) and then dried over MgSO₄, filtered and concentrated in vacuo to give the product as a brown oil. Yield 0.65 g, 45%.

Step 5: Preparation of 4-(5-Oxo-3-pyrazin-2-yl-2,5-dihydro-pyrazol-1-yl)-N-(1,2,2,6,6-pentamethyl-piperidin-4-yl)-benzamide

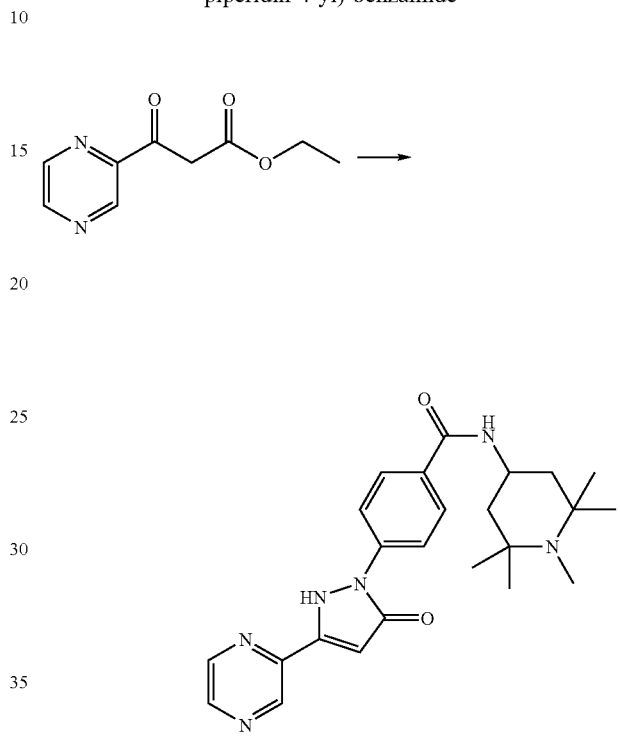

3-Oxo-3-pyrazin-2-yl-propionic acid, ethyl ester (78 mg) and 4-hydrazino-N-(1,2,2,6,6-pentamethyl-piperidin-4-yl)-benzamide (141 mg) were dissolved in ethanol (3.5 ml) and acetic acid (0.5 ml) and the solution stirred at 65° C. for 2 h. Concentration in vacuo and purification by HPLC gave the expected product. LC/MS: main peak is product (m/z: 434)

Example 2

4-(3-Isoxazol-5-yl-5-oxo-2,5-dihydro-pyrazol-1-yl)-N-(1,2,2,6,6-pentamethyl-piperidin-4-yl)-benzamide

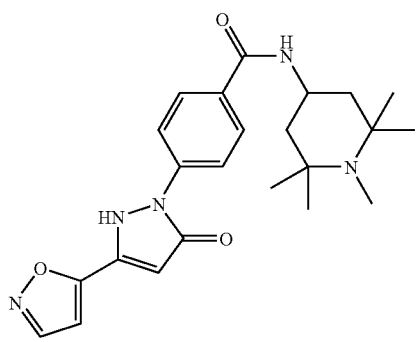

Step 1: Preparation of 3-Isoxazol-5-yl-3-oxo-propionic acid ethyl ester

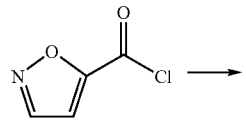

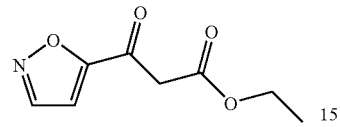

To a stirred solution of diethyl malonate (2.6 ml, 2.74 g) in THF (40 ml) under an atmosphere of nitrogen at −60° C. was added nbutyl lithium (2.5 M, 18.9 ml) dropwise over 15 mins, keeping the temperature constant. The reaction became a cloudy white colour from the formation of the di-lithium salt then became yellowish. After 10 mins, the reaction was cooled to −78° C., when a solution of Isoxazole-5-carbonyl chloride (1 g) in THF (10 ml) was added dropwise over 15 mins. The reaction then warmed to −45° C. and stirred for 1 h, the solution had gone pale brown. The reaction was then poured into 1M HCl solution (50 ml) with stirring and extracted with CH$_2$Cl$_2$ (2×150 ml). The combined organic layers were washed with sat. NaCO$_3$ soln (1×30 ml), dried over MgSO$_4$, filtered and concentrated in vacuo to give the product as a pale oil which was used as such in the next step. Yield 1.1 g, 35.1%.

Step 2: Preparation of 4-(3-Isoxazol-5-yl-5-oxo-2,5-dihydro-pyrazol-1-yl)-N-(1,2,2,6,6-pentamethyl-piperidin-4-yl)-benzamide

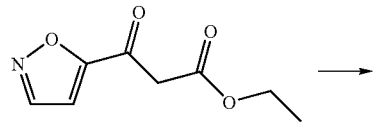

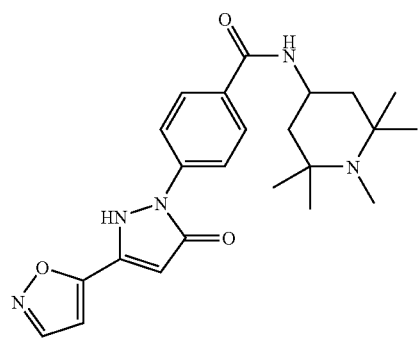

3-Isoxazol-5-yl-3-oxo-propionic acid ethyl ester (49 mg) and 4-Hydrazino-N-(1,2,2,6,6-pentamethyl-piperidin-4-yl)-benzamide (93 mg) were dissolved into ethanol (2.5 ml) and acetic acid (0.3 ml) and the solution stirred at 65° C. for 2 h. Concentration in vacuo and purification by HPLC gave the expected product. LC/MS: main peak is product (m/z: 424.3)

The compound of Example 2 had activity rating * in the HTRF assay described below.

Example 3

4-(3-Furan-2-yl-4-methyl-5-oxo-2,5-dihydro-pyrazol-1-yl)-N-(1,2,2,6,6-pentamethyl-piperidin-4-yl)-benzamide

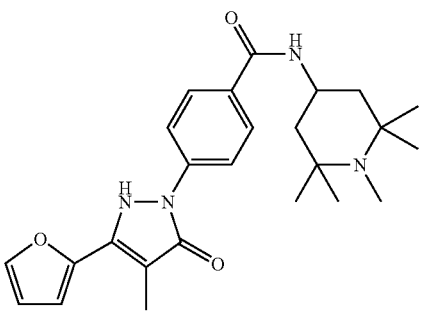

Step 1: Preparation of 3-furan-2-yl-2-methyl-3-oxo-propionic acid ethyl ester

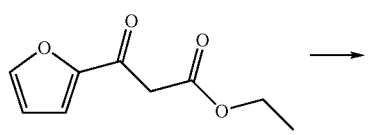

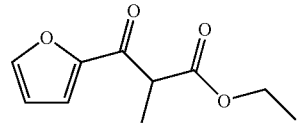

In a flask were placed ethyl 3-(2-furyl)-3-oxopropanoate (0.5 g), iodomethane (0.14 ml), finely ground potassium carbonate (0.75 g) and acetone (5 ml). The mixture was stirred at reflux for 2 h. A further portion of iodomethane (0.9 mmol, 0.056 ml) and potassium carbonate (0.9 mmol, 0.12 g) were added and the mixture stirred at reflux for 1 h. The reaction mixture was filtered and concentrated under vacuum. Yield (0.5 g, 93%).

Preparation of 4-(3-Furan-2-yl-4-methyl-5-oxo-2,5-dihydro-pyrazol-1-yl)-N-(1,2,2,6,6-pentamethyl-piperidin-4-yl)-benzamide

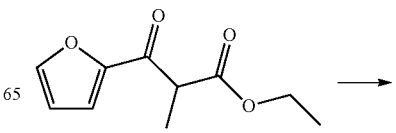

-continued

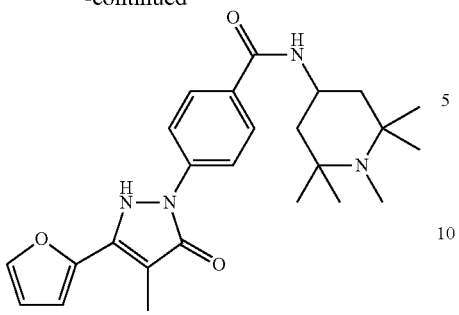

3-furan-2-yl-2-methyl-3-oxo-propionic acid ethyl ester (49 mg) and 4-Hydrazino-N-(1,2,2,6,6-pentamethyl-piperidin-4-yl)-benzamide (85 mg) in 0.5 ml of acetic acid were heated up at 65° C. for 2 h. Concentration in vacuo and purification by HPLC gave the expected product. MH+=437.3

The compound of Example 3 had activity rating * in the HTRF assay described below.

Example 4

4-(3-Furan-2-yl-4,4-dimethyl-5-oxo-4,5-dihydro-pyrazol-1-yl)-N-(1,2,2,6,6-pentamethyl-piperidin-4-yl)-benzamide Step 1: Preparation of 3-Furan-2-yl-2,2-dimethyl-3-oxo-propionic acid ethyl ester

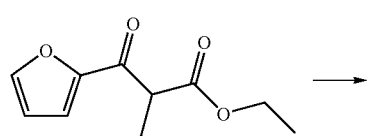

3-furan-2-yl-2-methyl-3-oxo-propionic acid ethyl ester (49 mg) was added sodium ethoxide (0.22 ml) and 0.5 ml ethanol. A solid precipitates. The solution was stirred at room temperature for 1 h, iodomethane was added and the suspension stirred at room temperature for 3 h. Concentration in vacuo and purification by HPLC gave the expected product.

Step 2: Preparation of 4-(3-Furan-2-yl-4,4-dimethyl-5-oxo-4,5-dihydro-pyrazol-1-yl)-N-(1,2,2,6,6-pentamethyl-piperidin-4-yl)-benzamide 3-Furan-2-yl-2,2-dimethyl-3-oxo-propionic acid ethyl ester (53 mg) and 4-Hydrazino-N-(1,2,2,6,6-pentamethyl-piperidin-4-yl)-benzamide (85 mg) in 0.5 ml of acetic acid were heated up at 65° C. for 2 h. Concentration in vacuo and purification by HPLC gave the expected product (MH+: 451.4)

Additional Examples

Further examples of compounds of the invention were synthesised by methods analogous to those of Examples 1-2 above. The structures of the synthesised compounds are shown in the following Table, together with their activity ratings in the HTRF assay described below.

TABLE 1

| Example | Z | W | R | MH+ | Activity Rating |
|---|---|---|---|---|---|
| 5 | Ph | H | CH₂CH₂CH₂N(Me)₂ | 365.2 | ** |
| 6 | Ph | H | (CH₂)₃-piperazine-N-CH₂-phenyl | 482.1 | * |
| 7 | Ph | H | 4-(2,2,6,6-tetramethyl-1-methylpiperidinyl) | 433.5 | ** |
| 8 | Ph | H | (CH₂)₄-pyrrolidinyl | 405.5 | *** |
| 9 | Ph | H | (CH₂)₃-NH-cyclohexyl | 419.5 | ** |
| 10 | 2-Pyridyl | H | CH₂CH₂CH₂N(Me)₂ | 366.5 | *** |
| 11 | 2-furyl | H | CH₂CH₂CH₂N(Me)₂ | 355.4 | *** |
| 12 | 3-Pyridyl | H | CH₂CH₂CH₂N(Me)₂ | 366.5 | ** |
| 13 | 2-Pyridyl | H | (CH₂)₃-NH-cyclohexyl | 420.5 | ** |
| 14 | 2-furyl | H | (CH₂)₃-NH-cyclohexyl | 409.5 | *** |
| 15 | 3-Pyridyl | H | (CH₂)₃-NH-cyclohexyl | 420.5 | ** |

TABLE 1-continued
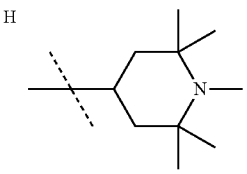
| Example | Z | W | R | MH+ | Activity Rating |
|---|---|---|---|---|---|
| 16 | 2-Pyridyl | H | 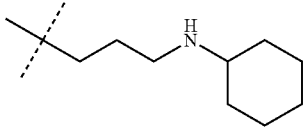 | 434.6 | *** |
| 17 | 3-furyl | H | CH₂CH₂CH₂N(Me)₂ | 355.5 | ** |
| 18 | 3-furyl | H | 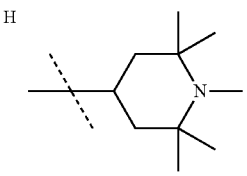 | 409.5 | *** |
| 19 | 2-furyl | H | 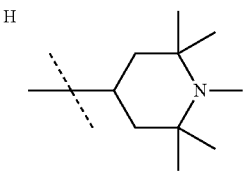 | 423.6 | *** |
| 20 | 3-furyl | H | 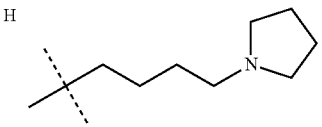 | 423.6 | ** |
| 21 | 2-furyl | H | 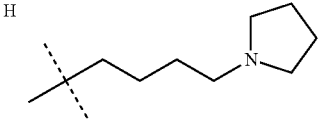 | 395.6 | ** |
| 22 | 3-furyl | H | 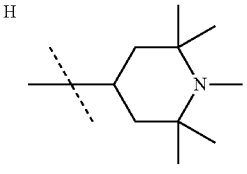 | 395.6 | ** |
| 23 | 3-Pyridyl | H | 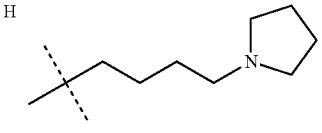 | 434.6 | ** |
| 24 | 2-Pyridyl | H | | 406.5 | *** |

TABLE 1-continued
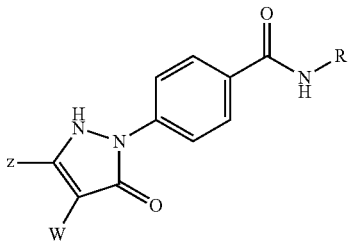
| Example | Z | W | R | MH+ | Activity Rating |
|---|---|---|---|---|---|
| 25 | 3-Pyridyl | H | 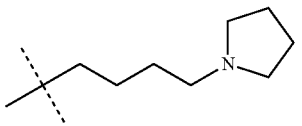 | 406.6 | ** |
| 26 | 3F-phenyl | H | CH$_2$CH$_2$CH$_2$N(Me)$_2$ | 383.5 | *** |
| 27 | 3F-phenyl | H | 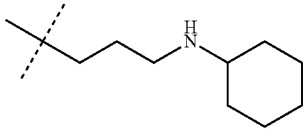 | 437.6 | ** |
| 28 | 3F-phenyl | H | 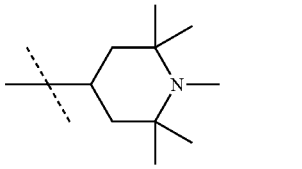 | 451.6 | *** |
| 29 | 2-pyrazinyl | H | 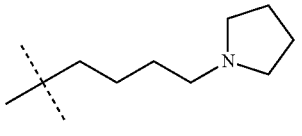 | 407.3 | ** |
| 30 | 2-pyrazinyl | H | CH$_2$CH$_2$CH$_2$N(Me)$_2$ | 367.3 | *** |
| 31 | 2-benzofuranyl | H | 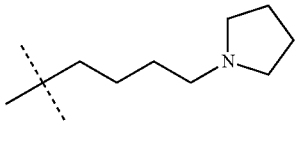 | 445.3 | ** |
| 32 | 2-benzofuranyl | H | CH$_2$CH$_2$CH$_2$N(Me)$_2$ | 405.3 | ** |
| 33 | 2-benzofuranyl | H | 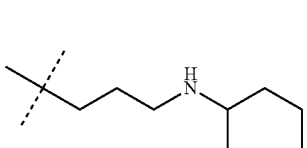 | 459.4 | ** |
| 34 | 2-benzofuranyl | H | 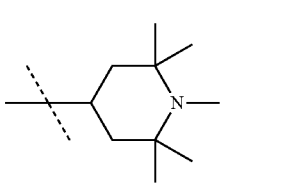 | 473.4 | ** |

TABLE 1-continued

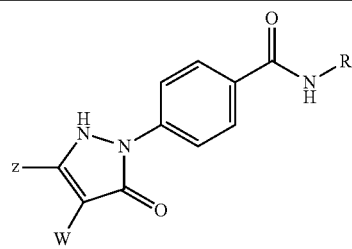

| Example | Z | W | R | MH+ | Activity Rating |
|---|---|---|---|---|---|
| 35 | 5-isoxazolyl | H | (2,2,6,6-tetramethylpiperidin-4-yl) | 424.3 | * |

Assay Protocols
The Use of BIAcore Biomolecular Interaction Analysis

Biotinylated human CD80 (hCD80-8T) is a recombinant soluble form of a membrane bound receptor molecule (CD80) which binds to CD28 to initiate T cell activation. The interaction between CD80 and CD28 has been extensively investigated (Collins et al, 2002). Biotinlyated human HLA-A2-tax is the recombinant soluble form of a membrane bound receptor molecule that has been used in this example as a control protein, and is not expected to interact with the compounds.

The BIAcore S51™ system was used for screening the compounds of Examples 1-4 above. A series S sensor chip CM5 was docked onto the BIAcore S51™. Streptavidin was coupled to the carboxymethyl surface using standard amine coupling. The chip surface was activated with 0.2M EDC/0.05M NHS, followed by binding of streptavidin (0.25 mg/ml in 10 mM sodium acetate pH 5.0) and saturation of unoccupied sites with 1 M ethylenediamine.

The BIAcore S51 sensor chip has two separate sensor spots for immobilisation of proteins. hCD80-8T was immobilised on the streptavidin-coated surface of one sensor spot until a response of approximately 3000 RU was observed. A protein to control for non-specific binding of the compound was immobilised on a second sensor spot. The control protein used for these experiments was a biotinylated, soluble form of the human HLA protein.

Dilution series of compounds (1000 nM-0.05 nM) were prepared in running buffer (10 mM, pH 7.4, 150 mM NaCl, 0.005% P20; 5% DMSO).

BIAcore S51™ was run at a flow rate of 30 μl/min using running buffer. Compounds and DMSO standard solutions for correction of data for solvent effects were injected. Data were recorded automatically and were analysed using BIAcore S51 Evaluation software.

The interaction between CD80 and the endogenous protein ligand (CD28) is highly specific, but relatively weak, with a $K_D$ of 4750 nM, and an off-rate of greater than 0.2 s$^{-1}$. The compounds of Examples 7, 11 & 18-21 have greater affinity and longer residence times on CD80 than CD28, having $K_D$S of less than 100 nM, and off-rates of 2×10$^{-2}$, indicating that the pyrazolones will be able to compete effectively with the endogenous ligand. The pyrazolones showed no detectable interaction with the control protein.

REFERENCES

Collins A V et al., (2002) Immunity 17, 201-210 "The interaction properties of costimulatory molecules revisited"

Inhibition of Production of Interleukin-2 (IL-2) by Human Jurkat T Cells.

Method

Human Raji cells were dispensed at a concentration of 2×10$^5$ cells per well in RPMI-1640 medium supplemented with 10% fetal calf serum, 1% penicillin/streptomycin, 1% glutamine (RPMI medium) in a 96-well round bottom microtitre plate. Compounds under investigation (dissolved in 100% DMSO) were diluted to eight-fold the desired final concentration in RPMI medium and added to the required final concentration for a total volume of 200 μl per well. After 20 minutes incubation at 37° C., Jurkat T cells were added at a concentration of 2×10$^5$ cells per well. Monoclonal antibody to CD3 (UCHT1, R&D Systems) was added to the cultures at a final concentration of 1 μg per ml, and where indicated, monoclonal antibody to CD28 (CD28.2, BD-Pharmingen) was also added at a concentration of 2.5 μg per ml. Cells were cultured at 37° C. for 5 hours, after which the plates were centrifuged and the supernatants harvested for IL-2 ELISA assay using the IL-2 Eli-pair kit (DIACLONE Research, Besancon, France) according to the manufacturers instructions.

By way of example, the compound of Example 26 gave 52% inhibition at 30 μM.

Homogenous Time Resolved Fluorescence Assay

The examples described above were tested in a cell free Homogenous Time Resolved Fluorescence (HTRF) assay to determine their activity as inhibitors of the CD80-CD28 interaction.

In the assay, europium and allophycocyanin (APC) are associated with CD28 and CD80 indirectly (through antibody linkers) to form a complex, which brings the europium and APC into close proximity to generate a signal. The complex comprises the following six proteins: fluorescent label 1, linker antibody 1, CD28 fusion protein, CD80 fusion protein, linker antibody 2, and fluorescent label 2. The table below describes these reagents in greater detail.

| | |
|---|---|
| Fluorescent label 1 | Anti-Rabbit IgG labelled with Europium (1 μg/ml) |
| Linker antibody 1 | Rabbit IgG specific for mouse Fc fragment (3 μg/ml) |
| CD28 fusion protein | CD28 - mouse Fc fragment fusion protein (0.48 μg/ml) |
| CD80 fusion protein | CD80 mouse Fab fragment (C215) fusion protein (1.9 μg/ml) |
| Linker antibody 2 | GαMκ-biotin: biotinylated goat IgG specific for mouse kappa chain (2 μg/ml) |
| Fluorescent label 2 | SA-APC: streptavidin labelled allophycocyanin (8 μg/ml) |

On formation of the complex, europium and APC are brought into proximity and a signal is generated.

Non-specific interaction was measured by substituting a mouse Fab fragment (C215) for the CD80 mouse Fab fragment fusion protein (1.9 μg/ml). The assay was carried out in black 384 well plates in a final volume of 30 μl. Assay buffer: 50 mM Tris-HCl, 150 mM NaCl pH7.8, containing 0.1% BSA (w/v) added just prior to use.

Compounds were added to the above reagents in a concentration series ranging between 100 μM-1.7 nM. The reaction was incubated for 4 hours at room temperature. Dual measurements were made using a Wallac Victor 1420 Multilabel Counter. First measurement: excitation 340 nm, emission 665 nm, delay 50 μs, window time 200 μs. second measurement excitation 340 nm, emission 615 nm, delay 50 μs, window time 200 μs. Counts were automatically corrected for fluorescence crossover, quenching and background. The EC50 activities of compounds tested are recorded as: EC50:*=>10 μM, =1-10 μM, *=<1 μM.

The invention claimed is:

1. A compound of formula (IA) or (1B) or a pharmaceutically or veterinarily acceptable salt thereof:

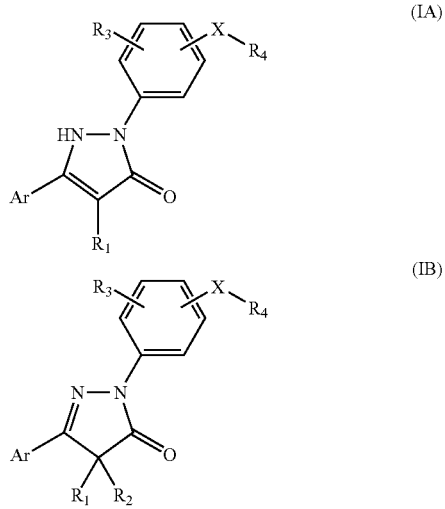

wherein
Ar represents an optionally substituted monocyclic or bicyclic aromatic or heteroaromatic group having from 5 to 10 ring atoms,
$R_1$ and $R_2$ independently represent H, or $C_1$-$C_6$ alkyl;
$R_3$ represents H; F; Cl; Br; $-NO_2$; $-CN$; $C_1$-$C_6$ alkyl optionally substituted by F or Cl; or $C_1$-$C_6$ alkoxy optionally substituted by F;
$R_4$ represents $-C(=O)NR_6R_7$, $-NR_7C(=O)R_6$, $-NR_7C(=O)OR_6$, $-NHC(=O)NR_7R_6$ or $-NHC(=S)NR_7R_6$ wherein
$R_6$ a radical of formula -(Alk)$_m$-Q wherein
m is 0 or 1
Alk is an optionally substituted divalent straight or branched $C_1$-$C_{12}$ alkylene, or $C_2$-$C_{12}$ alkenylene, or $C_2$-$C_{12}$ alkynylene radical or a divalent $C_3$-$C_{12}$ carbocyclic radical, any of which radicals may be interrupted by one or more $-O-$, $-S-$ or $-N(R_8)-$ radicals
wherein $R_8$ represents H or $C_1$-$C_4$ alkyl, $C_3$-$C_4$ alkenyl, $C_3$-$C_4$ alkynyl, or $C_3$-$C_6$ cycloalkyl, and
Q represents $NR_9R_2$ wherein the $R_9$ substituents form a ring when taken together with the nitrogen to which they are attached; or heterocyclic group; and
$R_7$ represents H or $C_1$-$C_6$ alkyl; or when taken together with the atom or atoms to which they are attached $R_6$ and $R_7$ form a monocyclic heterocyclic ring having 5, 6 or 7 ring atoms; and
X represents a bond or a divalent radical of formula $-(Z)_n$-(Alk)- or -(Alk)-$(Z)_n$— wherein Z represents $-O-$, $-S-$ or $-NH-$, Alk is as defined in relation to $R_6$ and n is 0 or 1.

2. A compound as claimed in claim 1 wherein $R_1$ in compounds (IA) and each of $R_1$ and $R_2$ in compounds (IB) is other than hydrogen.

3. A compound as claimed in claim 1 wherein $R_6$ represents a radical of formula -(Alk)$_m$-Q wherein m is 1, Alk is $-CH_2-$, $CH_2CH_2-$, $-CH_2CH_2CH_2-$, or $-CH_2CH(CH_3)CH_2-$, or a divalent cyclopropylene, cyclopentylene or cyclohexylene radical, optionally substituted by OH, oxo, $CF_3$, methoxy or ethoxy, and Q represents furyl, thienyl, piperidyl, or piperazinyl group.

4. A compound as claimed in claim 1 wherein $R_7$ represents hydrogen, methyl, ethyl, n- or iso-propyl, n-, sec- or tert-butyl; or when taken together with the atom or atoms to which they are attached $R_6$ and $R_7$ form a monocyclic heterocyclic ring having 5, 6 or 7 ring atoms.

5. A compound as claimed in claim 1 wherein Ar is optionally substituted phenyl, 2-, 3-, or 4-pyridyl, 2-, or 3-furyl, 2-, or 3-thienyl, benzfur-2-yl, or benzthien-2-yl.

6. A compound as claimed in claim 1 wherein Ar is substituted by F, Cl, methyl, methoxy, or methylenedioxy.

7. A compound as claimed in claim 1 wherein Ar is 3-fluorophenyl, or 2- or 3-furyl.

8. A compound as claimed in claim 1 wherein $R_3$ is H, F, Cl, methyl, methoxy, or methylenedioxy.

9. A compound as claimed in claim 1 wherein X is a bond, or a $-CH_2-$ or $-CH_2CH_2-$ radical.

10. A compound as claimed in claim 1 which is of formula (IC) or a pharmaceutically or veterinarily acceptable salt thereof:

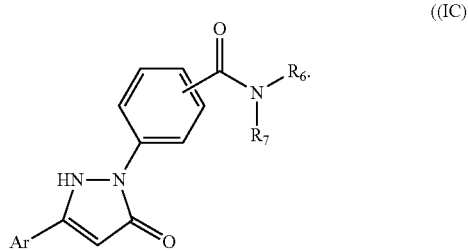

11. A compound as claimed in claim 10 wherein the radical —C(=O)NR$_6$R$_7$ is in the 4-position of the phenyl ring.

12. A compound as claimed in claim 10 wherein R$_7$ is hydrogen and R$_6$ is -AlkNR$_9$R$_9$ wherein the R$_9$ groups are as defined in claim 1.

13. A pharmaceutical or veterinary composition comprising a compound as claimed in claim 1 together with a pharmaceutically or veterinarily acceptable excipient or carrier.

14. A composition according to claim 13 wherein the compound is in an amount effective for treatment of conditions which benefit from immunomodulation.

15. A medicament for the treatment of conditions which benefit from immunomodulation comprising an effective amount of the compound according to claim 1 together with a pharmaceutically or veterinarily acceptable excipient or carrier; wherein the conditions are selected from rheumatoid arthritis, psoriasis, multiple sclerosis, and diabetes.

16. A method of immunomodulation in mammals, including humans, comprising administration to a mammal in need of such treatment an immunomodulatory effective dose of a compound as claimed in claim 1.

* * * * *

UNITED STATES PATENT AND TRADEMARK OFFICE
CERTIFICATE OF CORRECTION

PATENT NO.         : 8,163,757 B2
APPLICATION NO.    : 12/874280
DATED              : April 24, 2012
INVENTOR(S)        : Ian Richard Matthews Page 1 of 1

It is certified that error appears in the above-identified patent and that said Letters Patent is hereby corrected as shown below:

In the Claims

Column 26, Claim 1, Line 14:
Please delete "represents $NR_9R_2$ wherein" and replace with -- represents $NR_9R_9$ wherein --

Signed and Sealed this
Twenty-fourth Day of December, 2013

Margaret A. Focarino
*Commissioner for Patents of the United States Patent and Trademark Office*